United States Patent [19]

Laurent et al.

[11] Patent Number: 4,738,957
[45] Date of Patent: Apr. 19, 1988

[54] ESTRIOL ESTERS

[75] Inventors: Henry Laurent; Dieter Bittler; Sybille Beier; Walter Elger, all of Berlin, Fed. Rep. of Germany

[73] Assignee: Schering Aktiengesellschaft, Berlin and Bergkamen, Fed. Rep. of Germany

[21] Appl. No.: 842,691

[22] Filed: Mar. 21, 1986

[30] Foreign Application Priority Data

Mar. 21, 1985 [DE] Fed. Rep. of Germany ....... 3510555

[51] Int. Cl.$^4$ ............................ A61K 31/56; C07J 1/00
[52] U.S. Cl. .................................. 514/182; 514/170; 260/397.5
[58] Field of Search ...................... 260/397.5; 514/170, 514/182

[56] References Cited

U.S. PATENT DOCUMENTS 2,945,048 7/1960 Huffman .......................... 260/397.5
2,949,476 8/1960 Tyner .............................. 260/397.5
4,681,875 7/1987 Laurent .

OTHER PUBLICATIONS

Chem. Pharm. Bull. vol. 11, pp. 510–514 (1963) Tsuneda et al.
Acta Chem. Scand. 22, pp. 254–264 (1968).

Primary Examiner—Leonard Schenkman
Assistant Examiner—Joseph A. Lipovsky
Attorney, Agent, or Firm—Millen & White

[57] ABSTRACT

Estriol esters of Formula I

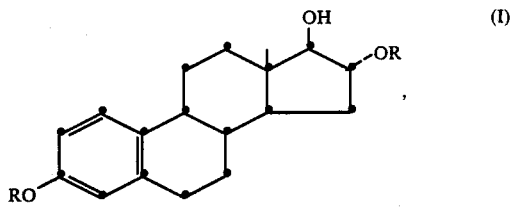

wherein
R is, in each case, the residue of an aliphatic monocarboxylic acid of 3–10 carbon atoms,
surpass estriol in strength and duration of estrogen activity.

18 Claims, No Drawings

ESTRIOL ESTERS

BACKGROUND OF THE INVENTION

This invention relates to novel estriol esters, to processes for their production, and to pharmaceutical preparations containing them.

Estriol, 1,3,5(10)-estratriene-3,16α,17β-triol, is an important natural estrogen. It is also utilized as the active ingredient in preparations for estrogen substitution in cases of estrogen deficiency, for example in postmenopausal women. Since estriol is very rapidly eliminated from the body, it must be administered in short intervals (one to three times daily).

Several esters of estriol have also been described in the literature, for example estriol triesters, 16,17-diesters and 16-monoesters in Chem. Pharm. Bull. 11: 510–514 (1963), as well as 3-acetate, 3,16-diacetate, and 16,17-diacetate in Acta Chem. Scand. 22: 254 (1968). With the exception of estriol succinate, which must be administered three times daily, no estriol esters have been utilized as medicines.

SUMMARY OF THE INVENTION

It is an object of this invention to provide new esters of estriol having improved properties.

Upon further study of the specification and appended claims, further objects and advantages of this invention will become apparent to those skilled in the art.

These objects have been attained by providing estriol esters of Formula I

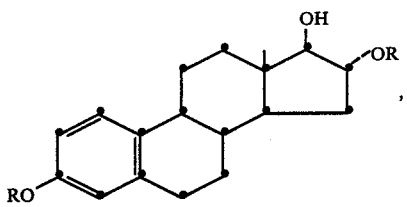

wherein R is, in each case, the residue of an aliphatic monocarboxylic acid of 3–10 carbon atoms.

The 3,16α-diesters of estriol with monocarboxylic acids of 3–10 carbon atoms, not disclosed heretofore, surpass estriol in potency and duration of estrogen activity.

DETAILED DISCUSSION

The ester residues R in Formula I are preferably identical and are derived from an aliphatic monocarboxylic acid. Preferred ester residues R are those of propionic acid, butyric acid, isobutyric acid, pivalic acid, valeric acid, caproic acid, enanthic acid, octanoic and decanoic acid. All other generically included acyl groups (e.g., alkanoyl groups) are also included, e.g., residues of nonoic acids; including all isomers thereof.

The estrogenic activity and depot properties of the novel estriol esters were determined in comparison with estriol ($E_3$) in a modified uterus growth test according to Rubin on ovariectomized rats [Endocrinology 49: 429–439 (1951)].

Adult ovariectomized rats weighing about 150 g, 6 animals per dosage group, are treated once with the respective test or reference compound (estriol). The day of administering the compound is considered day 1 ($d_1$) of the experiment. The compounds are dissolved in a mixture of benzyl benzoate+castor oil in a ratio of 4:6, and the daily dose is administered subcutaneously (s.c.) in a volume of 0.2 ml. A control group receives only 0.2 ml of vehicle.

Effective estrogens result in characteristic changes at the vaginal epithelium in ovariectomized rats. Strong proliferation of vaginal epithelium occurs, and the superficial cell layers are cornified. Vaginal smears are taken once darly. The smear images are evaluated cytologically.

Differentiation is made among the following cycle stages:

1 = diestrus (leukocytes and nucleated epithelium cells),
2 = proestrus (nucleated epithelium cells),
3 = estrus (anucleated cornified plaques),
4 = metestrus (anucleated cornified plaques, leukocytes, epithelium cells).

For determining the duration of estrogen activity on the vagina, the period is recorded, in days, on which estrus is maintained.

It can be seen from Table 1 that the animals remain in estrus for one day upon administration of estriol ($E_3$); estrus is maintained for 4, 10, and 30 days, respectively, after administration of equimolar amounts of $E_3$ diacetate, $E_3$ dipropionate and $E_3$ dihexanoate.

TABLE 1

Duration of Estrogen Effect on Vagina after One-Time Injection (s.c.) of Estriol ($E_3$) and, Respectively, One-Time Injection of Various 3,16-Diesters in Ovariectomized Rats in Equimolar Doses

| Compound | Estrus |
| --- | --- |
| Estriol ($E_3$), 100 μg s.c. | 1 Day |
| $E_3$ Diacetate, 129 μg s.c. | 4 Days |
| $E_3$ Dipropionate, 139 μg s.c. | 10 Days |
| $E_3$ Dihexanoate, 168 μg s.c. | 30 Days |

Table 2 indicates the chronological course of estriol ($E_3$) serum concentration in pmol/l after a one-time injection (s.c.) of estriol ($E_3$) and respectively one-time injection (s.c.) of various $E_3$ 3,16-diesters in ovariectomized rats.

Blood is drawn from the animals on the first day, 2 hours prior to injection; on the 5th, 10th, 15th, 20th, 25th and 30th day after injection in order to determine the serum $E_3$ concentration by means of RIA (radioimmunoassay).

Table 2 reveals that, after administration of the novel estriol 3,16-diesters, the $E_3$ concentration measured by radioimmunology is 3–7 times higher than after equimolar administration of estriol ($E_3$), and 2–4 times higher than after equimolar administration of the conventional $E_3$ diacetate. Increased $E_3$ concentrations are observed in the novel diesters up to 30 days after administration, in estriol and in $E_3$ diacetate only for 8 days after administration.

TABLE 2

Chronological Course of $E_3$ Serum Concentration (pmol/l) after One-Time Injection (s.c.) of Estriol ($E_3$) and Respectively One-Time Injection (s.c.) of Various 3,16-Diesters in Ovariectomized Rats in Equimolar Doses

| Compound | Day 1* | Day 5 | Day 10 | Day 15 | Day 20 | Day 25 | Day 30 |
|---|---|---|---|---|---|---|---|
| Estriol ($E_3$), 100 μg s.c. | 37.2 | 63.6 | Day 8: 57.0 | | | | |
| $E_3$ Diacetate, 129 μg s.c. | 37.0 | 139.0 | 56.8 | | | | |
| $E_3$ Dipropionate, 139 μg s.c. | 44.2 | 460.3 | 134.7 | 37.5 | | | |
| $E_3$ Dihexanoate, 168 μg s.c. | 43.5 | 172.3 | 198.3 | 138.5 | 97.8 | 94.3 | 87.5 |
| Solvent Control, s.c. | 39.9 | 39.8 | 39.3 | 37.1 | 36.7 | 36.0 | 50.3 |

*Two hours prior to injection

It can be seen from the results of the animal tests that potency of activity as well as duration of efficacy are increased by the esterification of estriol according to this invention.

A metabolically stabilized form of a natural estrogen is obtained by esterifying estriol in the 3,16-position per this invention. It has variegated uses in medicine inpatients, e.g., mammals including humans. Although the novel esters can also be administered orally, the parenteral method of administration is preferred because there the advantages of the novel esters are particularly apparent. By parenteral administration, initial liver passage and thereby rapid metabolzation are precluded. Furthermore, damaging hepatic estrogen effects are avoided by parenteral administration, such as, for example, a rise in clotting factors, increase in hormone-transporting proteins, increase in angiotensinogens, and a shift in the lipoprotein equilibrium.

Primary areas of usage of the novel estriol esters are substitution of estrogen in postmenopausal women suffering from climacteric deficiency symptoms, such as hot flashes, osteoporosis, atrophy of skin and genitals; furthermore, fertility control in women; and gynecological indications, such as, for example, vaginal atrophy, kraurosis vulvae, etc.

The quantity of the novel estriol esters to be administered varies within a wide range and can include any effective amount. Typically, the unit quantity is 1-100 mg, depending on the condition to be treated, the type of administration, and frequency of administration.

The novel esters are especially suitable as a pro-drug of estriol for the preparation of injectable or implanatable depot preparations. They also exhibit the advantage over orally administrable preparations that a single injection suffices for one or several months whereas, for example, tablets must be taken daily. Duration of the depot effect depends on the chain length and amount of the ester as well as on the type of carrier substance that releases the active agent. Generally, the duration will be in the range of 10-30 days, but longer or shorter times can also be achieved.

Suitable carrier compounds are physiologically compatible diluents wherein the active agents can be dissolved or suspended. An example for a diluent is water, with or without addition of electrolyte salts or thickeners. Thus, the depot formulation can be, for example, an aqueous microcrystalline suspension.

Oils are also used very frequently as diluents, with or without the addition of a solubilizer, of a surfactant, or of a suspension or emulsifying agent. Examples of oils utilizable include, in particular, olive oil, peanut oil, cottonseed oil, soybean oil, castor oil, and sesame oil. Examples of solubilizers are especially benzyl alcohol and benzyl benzoate. A preferred mixture comprises 6 parts by weight of castor oil and 4 parts by weight of benzyl benzoate.

When using the novel estriol esters as depot contraceptives, the novel esters can be combined with a depot gestagen or a gestagen to be administered orally, as is conventional, per se. The combined usage can be effected simultaneously, or staggered in time. Thus, a depot estrogen of Formula I and a depot gestagen can be combined, for example, into a one-month injection. Suitable as the depot gestagen for an oily solution is, for example, norethisterone enanthate and, for a microcrystalline suspension, medroxyprogesterone acetate.

Depending on the desired duration of activity, about 3 to 100 mg of the novel depot (i.e., controlled or sustained release) estrogen can be combined with 30 to 300 mg of a depot gestagen.

It is also possible to inject the depot eestrogen of this invention and to administer orally daily a conventional gestagen, such as norethisterone, norgestrel, levonorgestrel or cyproterone acetate.

Implantation preparations can contain the active agent in combination with inert materials, e.g., biodegradable polymers. The active ingredients can also be processed into implants with silicone rubber.

Except for the use of the novel esters of this invention, use of the foregoing estrogen-containing medicaments is generally per se known and discussed, e.g., in Aota. Obstet. Gynecol. Scand. Suppl. 65 (1977) 27.

The compounds are generally useful for the same purposes as and analogous to the known estrogenic agent Progynon ® or Progynova ®.

Doses for a given host can be determined using conventional considerations, e.g., by customary comparison of the differential activities of the subject compound and of a known agent, e.g., by means of an appropriate, conventional pharmacological protocol.

The novel compounds of Formula I can be prepared according to a process characterized by conventionally esterifying 16α-hydroxyestrone of Formula II

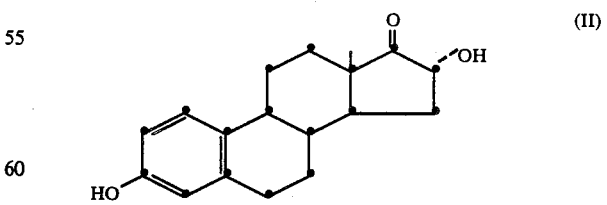

(II)

in the 3- and 16-positions and subsequently reducing the 17-ketone.

Esterification of the hydroxy groups in the 3- and 16-positions of the 16α-hydroxyestrone can be effected conventionally with the corresponding monocarboxylic acid RCOOH or a derivative, especially the anhydride or chloride of the monocarboxylic acid, in the presence of a base. Especially suitable bases are tertiary amines, such as pyridine, 4-dimethylaminopyridine, collidine, triethylamine, or mixtures of these amines. The subsequently performed reduction of the 17-ketone is likewise conducted according to known methods. A preferred method is reduction with lithium tri-tert-butoxyaluminohydride or sodium borohydride in anhydrous tetrahydrofuran at room temperature.

The starting compound of Formula II is known (J. Am. Soc. 82 (1960) 6143).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight; unless otherwise indicated.

EXAMPLE 1

(a) A solution of 1.0 g of 3,16α-dihydroxy-1,3,5(10)-estratrien-17-one in 5 ml of pyridine is combined with 2.5 ml of propionic anhydride and maintained at room temperature for 22 hours. The reaction mixture is poured into ice water, the resultant precipitate is filtered off, washed with water, and taken up in dichloromethane. After drying over sodium sulfate, the solvent is evaporated under vacuum and the residue chromatographed on silica gel with a pentane-diethyl ether gradient (0–50% diethyl ether), thus obtaining 640 mg of 3,16α-dipropionyloxy-1,3,5(10)-estratrien-17-one.

(b) 600 mg of 3,16α-dipropionyloxy-1,3,5(10)-estratrien-17-one is dissolved in 12 ml of tetrahydrofuran. The solution is combined with 600 mg of lithium tri-tert-butoxyaluminohydride and the reaction mixture is stirred for one hour at room temperature. The mixture is diluted with diethyl ether, washed with 1-molar sulfuric acid and water, and the organic phase is dried over sodium sulfate. Then the solution is evaporated to dryness; the residue is chromatographed on silica gel with a pentane-diethyl ether gradient (0–100% diethyl ether). The fractions containing the product are evaporated together. The residue yields, after recrystalization from hexane, 260 mg of 3,16α-dipropionyloxy-1,3,5(10)-estratrien-17β-ol, mp 118° C. $[\alpha]_D = +100°$ (in trichloromethane).

EXAMPLE 2

(a) A solution of 2.0 g of 3,16α-dihydroxy-1,3,5(10)-estratrien-17-one in 10 ml of pyridine and 5 ml of butyric anhydride is allowed to stand at room temperature for 15 hours with the addition of 100 mg of 4-dimethylaminopyridine. The reaction mixture is diluted with diethyl ether, washed with water, dried over sodium sulfate, and evaporated. The residue is chromatographed on silica gel with a pentane-diethyl ether gradient (0–30% diethyl ether), yielding 1.2 g of 3,16α-dibutyryloxy-1,3,5(10)-estratrien-17-one as an oil.

(b) 1.2 g of 3,16α-dibutyryloxy-1,3,5(10)-estratrien-17-one is reacted and worked up—as described in Example 1(a). After chromatography, 460 mg of 3,16α-dibutyryloxy-1,3,5(10)-estratrien-17β-ol is obtained as an oil. $[\alpha]_D = +94°$ (in trichloromethane).

EXAMPLE 3

(a) 2.0 g of 3,16α-dihydroxy-1,3,5(10)-estratrien-17-one is reacted with valeric anhydride under the reaction conditions described in Example 2(a) and purified, thus obtaining 1.1 g of 3,16α-divaleryloxy-1,3,5(10)-estratrien-17-one.

(b) Under the conditions disclosed in Example 2(b), 1.1 g of 3,16α-divaleryloxy-1,3,5(10)-estratrien-17-one yields 385 mg of 3,16α-divaleryloxy-1,3,5(10)-estratrien-17β-ol as an oil. $[\alpha]_D = +88°$ (in trichloromethane).

EXAMPLE 4

(a) 1.0 g of 3,16α-dihydroxy-1,3,5(10)-estratrien-17-one is reacted with caproic anhydride under the reaction conditions set forth in Example 2(a) and purified, yielding 750 mg of 3,16α-dihexanoyloxy-1,3,5(10)-estratrien-17-one.

(b) 750 mg of 3,16α-dihexanoyloxy-1,3,5(10)-estratrien-17-one is converted to 240 mg of 3,16α-dihexanoloxy-1,3,5(10)-estratrien-17β-ol under the conditions described in Example 2(b). $[\alpha]_D = +76°$ (in trichloromethane).

EXAMPLE 5

(a) 2.0 g of 3,16α-dihydroxy-1,3,5(10)-estratrien-17-one is reacted—as described in Example 2(a)—but with decanoic anhydride within 42 hours and then purified, thus obtaining 1.3 g of 3,16α-didecanoyloxy-1,3,5(10)-estratrien-17-one as an oil.

(b) Under the reaction conditions disclosed in Example 2(b), 1.3 g of 3,16α-didecanoyloxy-1,3,5(10)-estratrien-17-one yields, after purification, 570 mg of 3,16α-didecanoyloxy-1,3,5(10)-estratrien-17β-ol as an oil. $[\alpha]_D = +64.2°$ (in chloroform).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An estriol ester of the formula

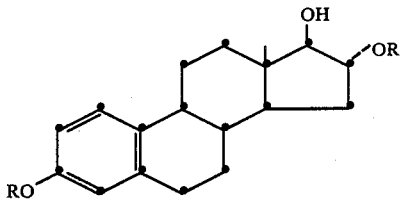

wherein R is, in each case, alkanoyl of 3–10 carbon atoms.

2. A compound of claim 1, wherein the R groups are identical.

3. 3,16α-Dipropionyloxy-1,3,5(10)-estratrien-17β-ol, a compound of claim 2.

4. 3,16α-Dibutyryloxy-1,3,5(10)-estratrien-17β-ol, a compound of claim 2.

5. 3,16α-Divaleryloxy-1,3,5(10)-estratrien-17β-ol, a compound of claim 2.

6. 3,16α-Dihexanoyloxy-1,3,5(10)-estratrien-17β-ol, a compound of claim 2.

7. 3,16α-Didecanoyloxy-1,3,5(10)-estratrien-17β-ol, a compound of claim 2.

8. A pharmaceutical composition comprising a compound of claim 1 and a carrier.

9. A pharmaceutical composition comprising 1–100 mg of a compound of claim 1 and a carrier.

10. A pharmaceutical composition of claim 8 adapted for parenteral administration.

11. A method of treating climacteric deficiency symptoms in a female comprising administering a compound of claim 1.

12. A method of claim 11, wherein the symptom is hot flashes, osteoporosis, or atrophy of skin or the genitals.

13. A method of claim 11, wherein the administration is parenterally.

14. A method of contraception comprising administering a compound of claim 1.

15. A method of treating a gynecological disorder comprising administering a compound of claim 1.

16. A method of claim 15, wherein the disorder is vaginal atrophy or praurosis vulvae.

17. A method of claim 15, wherein the administration is parenterally.

18. A method of treating a patient in need of estrogen comprising administering a compound of claim 1 in controlled release fashion whereby a depot estrogenic effect is achieved.

* * * * *